United States Patent [19]

Auel et al.

[11] 4,042,324
[45] Aug. 16, 1977

[54] PROCESS FOR INHIBITING THE CORROSIONS AND DEPOSITION OF BOILER SCALE IN WATER-CONVEYING SYSTEMS

[75] Inventors: Theodor Auel; Hannsjorg Ulrich, both of Erftstadt; Horst-Dieter Wasel-Nielen, Hurth-Hermulheim; Gero Heymer, Erftstadt, all of Germany

[73] Assignee: Hoechst Aktiengesellschaft, Frankfurt am Main, Germany

[21] Appl. No.: 654,885

[22] Filed: Feb. 3, 1976

[30] Foreign Application Priority Data

Feb. 8, 1975 Germany .............................. 2505435

[51] Int. Cl.$^2$ ......................... C02B 5/06; C23F 11/16
[52] U.S. Cl. ................................. 21/2.7 A; 21/2.5 A; 210/58; 252/82; 252/180; 252/389 A
[58] Field of Search ................ 252/389 A, 180, 82; 21/2.7 A, 2.5 A; 260/606.5 P, 606.5 F; 210/58

[56] References Cited

U.S. PATENT DOCUMENTS 3,630,790  12/1971  Schmidt et al. ................. 252/389 A Primary Examiner—Benjamin R. Padgett
Assistant Examiner—Irwin Gluck
Attorney, Agent, or Firm—Connolly and Hutz

[57] ABSTRACT

Corrosion and deposition of boiler scale in water-conveying systems are inhibited. To this end the water is admixed with at least one carboxy-alkane compound of phosphorus of the general formula:

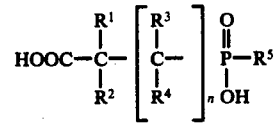

in which each of the substituents $R^1$, $R^2$, $R^3$, and $R^4$ stands for hydrogen or an alkyl group having from 1 to 4 carbon atoms, $R^5$ stands for hydrogen, an OH-group or an alkyl group having from 1 to 3 carbon atoms, and n stands for 0 or 1, or with at least one water-soluble salt thereof.

2 Claims, No Drawings

PROCESS FOR INHIBITING THE CORROSIONS AND DEPOSITION OF BOILER SCALE IN WATER-CONVEYING SYSTEMS

Inorganic polyphosphates have long been used up to-date as corrosion inhibitors in cooling-water cycles, although they are not entirely suitable for this. For example, it is necessary for the polyphosphates to be used within a relatively narrow pH-range, generally of from 6.5 up to 7. This in turn calls for the additional use of sulfuric acid. In addition to this, the water under circulation becomes increasingly loaded with sludge inasmuch as the polyphosphates undergo hydrolysis with the resultant formation of orthophosphates which together with the hardness-inducing salts in the water form difficultly soluble phosphates.

Attempts have also been made to use nitrogen-containing phosphonic acids, especially N-substituted oligo-phosphonic acids, as corrosion inhibitors in cooling-water cycles. These acids are, however, difficultly accessible which is disadvantageous. In addition to this, they tend to precipitate in the presence of an acid and then become inactive.

In German Specification "Offenlegungsschrift" 2,225,645, it is suggested that phosphonosuccinic acids of the general formula:

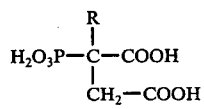

be used as agents inhibiting corrosion and the deposition of boiler scale.

These compounds can be made, for example, by the process disclosed in German Specification "Offenlegungsschrift" 2,015,068 which, however, is expensive and technically difficult to carry out.

It is therefore an object of the present invention to provide fully serviceable, readily accessible and inexpensive products which afford a good protection against corrosion in water-conveying systems.

In accordance with our present invention, we now unexpectedly provide a process permitting the phenomena or corrosion and deposition of boiler scale in water-conveying systems to be inhibited, which process comprises: admixing the water with one or more carboxyalkane compounds of phosphorus of the general formula:

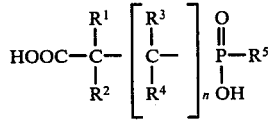

in which each of the substituents $R^1$, $R^2$, $R^3$ and $R^4$ stands for hydrogen or an alkyl group having from 1 to 4 carbon atoms, $R^5$ stands for hydrogen, an OH-group or an alkyl group having from 1 to 3 carbon atoms, and $n$ stands for 0 or 1, or with one or more water soluble salts thereof. The preferred representatives of the above compounds comprise more particularly: carboxymethane-phosphonic acid; 1-carboxy-ethane-1-phosphonic acid; 1-carboxy-ethane-2-phosphonic acid; 2-carboxy-propane-3-phosphonic acid; 1-carboxy-propane-2-phosphonic acid or methyl-(carboxyethyl)-phosphinic acid.

The compounds, which are used in accordance with the present invention, comprise more particularly phosphonic, phosphonous, and phosphinic acids, which are inexpensive and readily obtainable. Also beneficial is the fact that they do not decompose, even at the high temperatures which normally prevail inside heat exchanger systems. More especially, the compounds used in this invention are active within a very wide pH range, whereas a good deal of the inhibitors used heretofore become inactive in water having an alkalinity of more than pH 8. This a a value which is invariably established in open circulation systems unless provision is made for the additional use of an acid, for example. In other processes, e.g. in the electrolysis of alkali metal chlorides, alkali is very likely to penetrate into the water under circulation, which is hazardous. As already intimated above, the compounds used in the present invention remain fully active even at high pH-values, which is a further technically beneficial property.

The compounds which are added in accordance with the present invention to water enable the corrosion and deposition of boiler scale in water-conveying systems to be effectively inhibited, although some of them are not complex formers. The mechanism underlying this unexpected effect has not yet been identified. On the other hand, this property has long been held in the art to be typical of good complex formers.

The compounds of the present invention should be added in the form of free acid or a water-soluble salt thereof in proportions which are selected in accordance with requirements and preferably range from 5 to 100 grams, more preferably from 15 to 30 grams, per cubic meter of water under circulation.

It is also possible for the present inhibitors to be used in admixture with soluble zinc salts, dispersants or algicides, or for these latter substances to be additionally added to the water under circulation.

The following Examples illustrate the invention and the efficiency of the compounds used therein.

EXAMPLES 1 to 8:

The experiments were run in the laboratory with the use of a model apparatus in which a cooling medium was circulated. Specimens of unalloyed steel which each had a surface area of 45 cm² were placed in a cylindrical glass vessel filled with water of 80° C. Compressed air was introduced into the vessel by means of a pump of the kind used for an aquarium. The air caused the water to travel upwardly in the vessel, through two condensers, and a third coil condenser, wherein the water was contacted with jacket-heated steam and thereby heated from room temperature to 80° C, and then recycled to the cylindrical vessel. Evaporated water was automatically replaced by fresh water coming from a levelling vessel. In this testing method, it was an important requirement for the iron specimens to be always contacted with air-saturated water which accelerated corrosion.

The water used had an overall hardness of 22.7° dH (dH stands for German degree of hardness), a carbonate hardness of 9.9° dH and contained 65 ppm of Cl⁻ and 173 ppm of $SO_4^{2-}$.

A pH-value of 8.5 was found to establish in the water, which was kept free from sulfuric acid. The experiments were run over an average period of 120 hours. The rate of corrosion was determined by analysis. Analyzed was the iron which was dissolved or in the form of rust.

from 0.02 to 0.04 mm/annum, i.e. at a rate of 18–36 mg Fe/m² per hour.

| Example | n | R¹ | R² | R³ | R⁴ | R⁵ | Inhibitor | Rate of corrosion in mg Fe/m² |
|---|---|---|---|---|---|---|---|---|
| Comparative Ex. 1 | — | — | — | — | — | — | none | 1400 |
| Comparative Ex. 2 | 0 | —CH₂—CH₂—COOH | —CH₂—COOH | — | — | OH | $(OH)_2P(O)-C(CH_2COOH)(CH_2CH_2COOH)-COOH$ | 92.6 |
| 3 | 0 | H | H | — | — | OH | HOOC—CH₂—PO₃H₂ | 19.7 |
| 4 | 0 | H | CH₃ | — | — | OH | HOOC—CH(CH₃)—PO₃H₂ | 34.7 |
| 5 | 1 | H | H | H | H | OH | HOOC—CH₂—CH₂—PO₃H₂ | 8.3 |
| 6 | 1 | H | CH₃ | H | H | OH | HOOC—CH(CH₃)—CH₂—PO₃H₂ | 7.8 |
| 7 | 1 | H | H | H | CH₃ | OH | HOOC—CH₂—CH(CH₃)—PO₃H₂ | 31.5 |
| 8 | 1 | H | H | H | H | CH₃ | HOOC—CH₂—CH₂—P(O)(OH)—CH₃ | 39.5 |

The inhibitors tested were all used in a concentration of 20 ppm without any further addends. The results obtained are indicated in the Table hereinafter. The particulars indicated under the headings n and R¹ through R⁵ relate to the general formula of the compounds used in accordance with the present invention. Examples 1 and 2 are comparative Examples. The 1,2,4-tricarboxy-butane-2-phosphonic acid inhibitor employed in Example 2 is a corrosion inhibitor which has been described in German Specification "Offenlegungsschrift" 2,225,645.

EXAMPLE 9:

A system, in which about 1200 m³/h of water was circulated by pumping, was continuously supplied with the quantity of an aqueous solution of 1-carboxyethane-2-phosphonic acid which was necessary to maintain a 20 ppm concentration of inhibitor in the water under circulation. The water had an overall hardness of 38.5° dH, a carbonate hardness of 9.0° dH, and contained 115 ppm of Cl⁻ and 470 ppm of SO₄²⁻.

The pH was 8.1. The rate of corrosion was determined as usual by means of test coupons. During a 10 month testing period, corrosion occurred at a rate of

We claim:
1. A process for inhibiting the phenomena of corrosion and deposition of boiler scale in water-conveying systems, which comprises admixing the water with at least one carboxy-alkane compound of phosphorus of the general formula:

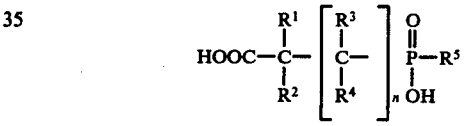

in which each of the substituents R¹, R², R³ and R⁴ stands for hydrogen or an alkyl group having from 1 to 4 carbon atoms, R⁵ stands for hydrogen, an OH—group or an alkyl group having from 1 to 3 carbon atoms, and n stands for 0 or 1, or with at least one water-soluble salt thereof.

2. The process as claimed in claim 1, wherein the water is admixed with at least one member selected from the group consisting of carboxy-methane-phosphonic acid; 1-carboxy-ethane-1-phosphonic acid; 1-carboxy-ethane-2-phosphonic acid; 2-carboxy-propane-3-phosphonic acid; 1-carboxy-propane-2-phosphonic acid; and methyl-(carboxyethyl)-phosphinic acid.

* * * * *